US011559633B2

(12) United States Patent
Kim et al.

(10) Patent No.: US 11,559,633 B2
(45) Date of Patent: *Jan. 24, 2023

(54) SYRINGE ADAPTER WITH SPINNING CONNECTOR

(71) Applicant: Becton Dickinson and Company Limited, Dun Laoghaire (IE)

(72) Inventors: Jayeon Kim, River Edge, NJ (US); Laurie Sanders, Glen Ridge, NJ (US); Yan Yevmenenko, New York, NY (US)

(73) Assignee: Becton Dickinson and Company Limited, Dun Laoghaire (IE)

(*) Notice: Subject to any disclaimer, the term of this patent is extended or adjusted under 35 U.S.C. 154(b) by 60 days.

This patent is subject to a terminal disclaimer.

(21) Appl. No.: 16/750,204

(22) Filed: Jan. 23, 2020

(65) Prior Publication Data
US 2020/0155770 A1 May 21, 2020

Related U.S. Application Data

(63) Continuation of application No. 15/178,883, filed on Jun. 10, 2016, now Pat. No. 10,561,802.

(60) Provisional application No. 62/174,783, filed on Jun. 12, 2015.

(51) Int. Cl.
*A61M 5/34* (2006.01)
*A61J 1/20* (2006.01)

(52) U.S. Cl.
CPC ............ *A61M 5/345* (2013.01); *A61J 1/2096* (2013.01); *A61M 5/347* (2013.01); *A61J 1/201* (2015.05)

(58) Field of Classification Search
CPC ...... A61M 5/345; A61M 5/347; A61J 1/2096; A61J 1/201
See application file for complete search history.

(56) References Cited

U.S. PATENT DOCUMENTS

| | | | |
|---|---|---|---|
| 8,336,587 B2 | 12/2012 | Rosenquist et al. |
| 8,523,838 B2 | 9/2013 | Tornqvist |
| 8,562,583 B2 | 10/2013 | Akerlund et al. |
| 8,827,978 B2 | 9/2014 | Ellstrom |
| 9,162,803 B2 | 10/2015 | Rosenquist |
| 9,309,020 B2 | 4/2016 | Helmerson et al. |
| 9,352,104 B2 | 5/2016 | Thorley et al. |
| 9,492,353 B2 | 11/2016 | Nord et al. |

(Continued)

FOREIGN PATENT DOCUMENTS

| | | |
|---|---|---|
| CN | 102869398 A | 1/2013 |
| CN | 204170096 U | 2/2015 |

(Continued)

*Primary Examiner* — Tasnim Mehjabin Ahmed
(74) *Attorney, Agent, or Firm* — The Webb Law Firm

(57) ABSTRACT

A syringe adapter includes a housing having a first end and a second end and defining an interior space, a seal arrangement received within the interior space of the housing, a connector body positioned adjacent the first end of the housing and configured to be connected with a syringe barrel with the connector body secured to the housing and rotatable relative to the housing in first and second directions, and a cannula secured to the connector body. The connector body is axially fixed relative to the housing. The seal arrangement is configured to cooperate with the cannula to provide a sealed transfer of fluids through the cannula to a mating connector.

18 Claims, 16 Drawing Sheets

(56) References Cited

U.S. PATENT DOCUMENTS

| | | |
|---|---|---|
| 10,238,576 B2 | 3/2019 | Garfield et al. |
| 10,441,507 B2 | 10/2019 | Sanders |
| 10,561,802 B2 * | 2/2020 | Kim ............... A61J 1/2096 |
| 2013/0072893 A1 | 3/2013 | Takemoto |
| 2014/0007973 A1 | 1/2014 | Akerlund et al. |
| 2014/0014210 A1 | 1/2014 | Cederschiold |
| 2014/0150925 A1 * | 6/2014 | Sjogren ............ A61M 5/1782 |
| | | 141/94 |
| 2014/0261877 A1 | 9/2014 | Ivosevic et al. |
| 2015/0123398 A1 | 5/2015 | Sanders |
| 2015/0126974 A1 | 5/2015 | Sanders et al. |
| 2015/0209568 A1 | 7/2015 | Rosenquist |
| 2016/0031614 A1 | 2/2016 | Rosenquist |
| 2016/0031620 A1 | 2/2016 | Rosenquist |
| 2016/0262982 A1 | 9/2016 | Cederschiold |
| 2017/0042768 A1 | 2/2017 | Nord et al. |

FOREIGN PATENT DOCUMENTS

| | | |
|---|---|---|
| EP | 3067037 A1 | 9/2016 |
| EP | 3134052 A1 | 3/2017 |
| EP | 3656367 A2 | 5/2020 |
| JP | 2001190658 A | 7/2001 |
| JP | 2013529478 A | 7/2013 |
| WO | 02066100 A2 | 8/2002 |
| WO | 2011150037 A1 | 2/2011 |
| WO | 2012002315 A1 | 1/2012 |
| WO | 2015069638 A1 | 5/2015 |
| WO | 2015069643 A1 | 5/2015 |
| WO | 2015164339 A1 | 10/2015 |

\* cited by examiner

SYRINGE ADAPTER WITH SPINNING CONNECTOR

CROSS-REFERENCE TO RELATED APPLICATION

The present application is a continuation of U.S. patent application Ser. No. 15/178,883, entitled "Syringe Adapter with Spinning Connector", filed Jun. 10, 2016, which claims priority to U.S. Provisional Patent Application Ser. No. 62/174,783, entitled "Syringe Adapter with Spinning Connector", filed Jun. 12, 2015, the entire disclosure of which is hereby incorporated by reference.

BACKGROUND OF THE INVENTION

Field of the Invention

The present invention relates to a syringe adapter and, more particularly, to a spinning connector for a syringe adapter.

Description of Related Art

Healthcare workers, such as pharmacists and nurses, can be subject to acute and long term health risks upon repeated exposure to drugs or solvents which might escape into the air during drug preparation, drug administration, and other similar handling. This problem is particularly serious when cytotoxins, antiviral drugs, antibiotics, and radiopharmaceuticals are concerned. The health risks faced by exposure to these drugs can include the development of cancer, reproductive problems, genetic conditions, and other serious concerns. Other hazardous areas may be sample taking, such as samples concerning virus infections or the like. When performing infusions, it is often necessary to inject a drug or other medical substance into the infusion fluid, inside an infusion bag or other infusion fluid container. This is often done by means of penetrating a septum or other fluid barrier of an injection port on the infusion bag or on the infusion fluid line with a needle of a syringe filled with the medical fluid in question. However, even before this, it may be necessary to transfer the medical fluid from a vial to a syringe and then from the syringe to a secondary container. In each of these steps, staff may be exposed to the medical fluid by means of contamination. Such contamination may be vaporized medical fluid or aerosol in the air. The contaminations may contaminate the staff through their lungs, or by vaporized medical fluid or aerosol in the air which condensates on the skin to thereafter penetrate the skin of the staff. Some medicaments are even known to penetrate protection gloves and, thereby, contaminate the staff.

Exposure to contaminations like this may, on a long term basis, give rise to high concentrations of medicaments in the blood or the human body of the staff as described above. It has been understood that, due to the many transferring steps between containers e.g., vials, syringes, infusion systems, etc., the risk for contamination during the actual insertion and retraction of a needle from the container, e.g., a vial, needs to be contained. Closed system transfer devices (CSTDs) have been developed to ensure that the medicament is contained in the transfer device during transfer of the medicament.

Generally, a CSTD includes a syringe adapter for connection to a syringe and an adapter for connection to a vial, a second syringe, or a conduit providing fluid access to the patient's circulatory system. According to one arrangement, the healthcare practitioner may reconstitute a powdered or lyophilized compound with saline or some other reconstitution medium by attaching the syringe to the vial via connection of the respective adapters, reconstituting the drug, aspirating the compound into the syringe, disconnecting the adapters, and then attaching the syringe to the fluid conduit through the respective adapters to a patient delivery device, such as an IV line or syringe for administration to the patient.

One type of an adapter that can be used in a CSTD has a first connector having a male or female luer-lock element that is arranged to be joined with a corresponding female or male luer-lock element of a second connector component. According to one aspect, the second connector component can be a patient delivery device, such as an IV line or a syringe. The luer-lock element can, thus, be screwed into and unscrewed from the corresponding luer-lock element. It is desirable to prevent an accidental or inadvertent unscrewing of the components, which could lead to the disconnection of the fluid passage. Such disconnection may entail a serious contamination risk for a patient and/or any other person in the vicinity of the disconnected medical connector. The issue of safety in administration of hazardous medical compounds is one that has been identified as being of critical importance by professional organizations and government agencies alike.

It is, therefore, desirable to provide an adapter for enabling fluid transfer between the first connector and the second connector by facilitating a positive connection of the connectors and avoiding inadvertent or accidental disconnection of the connectors.

SUMMARY OF THE INVENTION

According to one aspect, a syringe adapter includes a housing having a first end and a second end and defining an interior space, a seal arrangement received within the interior space of the housing, and a connector body positioned adjacent to the first end of the housing and configured to be connected with a syringe barrel. The connector body is secured to the housing and rotatable relative to the housing in first and second directions. The connector body is axially fixed relative to the housing. The syringe adapter further includes a cannula secured to the connector body, with the seal arrangement configured to cooperate with the cannula to provide a sealed transfer of fluids through the cannula to a mating connector.

The connector body may include a locking projection and the housing may include a retaining ring, where the locking projection engages the retaining ring to restrict axial movement of the connector body relative to the housing. The housing may define a recess adjacent to the retaining ring, with the recess of the housing receiving the locking projection. The locking projection and the retaining ring may each define an angled surface, with the angled surface of the locking projection configured to engage the angled surface of the retaining ring to bias the locking projection radially outward during connection of the locking projection to the retaining ring. The retaining ring may extend radially outward from the housing. The retaining ring may extend circumferentially around the housing. The connector body may include a plurality of locking projections.

The connector body may include a skirt extending in an axial direction, with the skirt of the connector body receiving the first end of the housing. The connector body may define an opening, with the locking projection extending radially inward from the skirt and positioned adjacent to the opening of the connector body. The connector body may be a different color than the housing. The cannula may be entirely positioned within the housing. The seal arrangement may be moveable within the housing, the seal arrangement comprising a membrane. The connector body may include a grip arrangement configured to be engaged by a user. The connector body may be a female luer connector.

In a further aspect, a syringe adapter includes a housing having a first end and a second end and defining an interior space. The housing further includes a retaining ring. The syringe adapter also includes a seal arrangement received within the interior space of the housing with the seal arrangement moveable within the housing and including a membrane, and a connector body positioned adjacent to the first end of the housing and configured to be connected with a syringe barrel. The connector body includes a locking projection that cooperates with the retaining ring of the housing to secure the connector body to the housing, with the connector body rotatable relative to the housing in first and second directions. The locking projection engages the retaining ring to restrict axial movement of the connector body relative to the housing. The syringe adapter also includes a cannula secured to the connector body, with the seal arrangement configured to cooperate with the cannula to provide a sealed transfer of fluids through the cannula to a mating connector.

The housing may define a recess adjacent to the retaining ring, the recess of the housing receiving the locking projection. The locking projection and the retaining ring each define an angled surface, with the angled surface of the locking projection configured to engage the angled surface of the retaining ring to bias the locking projection radially outward during connection of the locking projection to the retaining ring. The retaining ring may extend radially outward from the housing, with the retaining ring extending circumferentially around the housing. The connector body may include a skirt extending in an axial direction, with the skirt of the connector body receiving the first end of the housing, and with the skirt of the connector body defining an opening. The locking projection may extend radially inward from the skirt and may be positioned adjacent to the opening of the connector body. The connector body may include a grip arrangement configured to be engaged by a user, with the connector body being a different color than the housing.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

Figure 1:
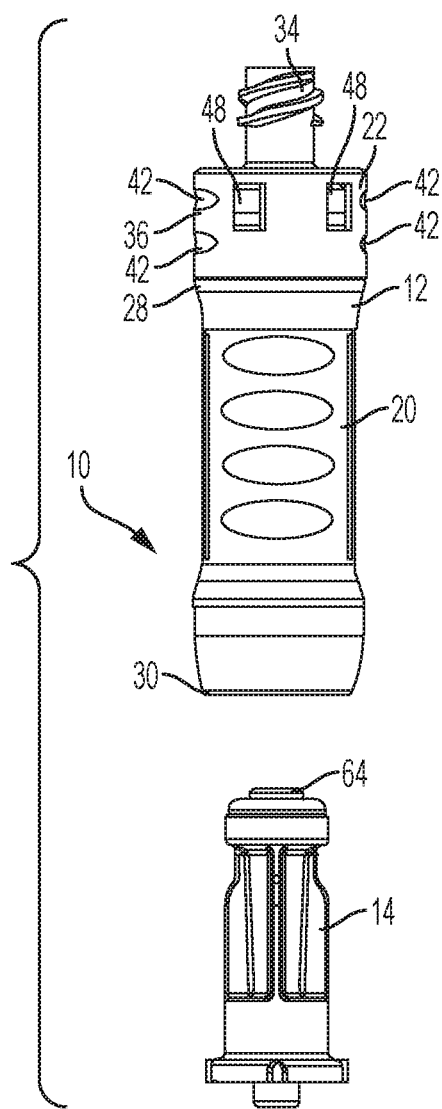
FIG. 1 is a front view of a syringe adapter and patient connector assembly according to one aspect of the present invention.
Figure 2:
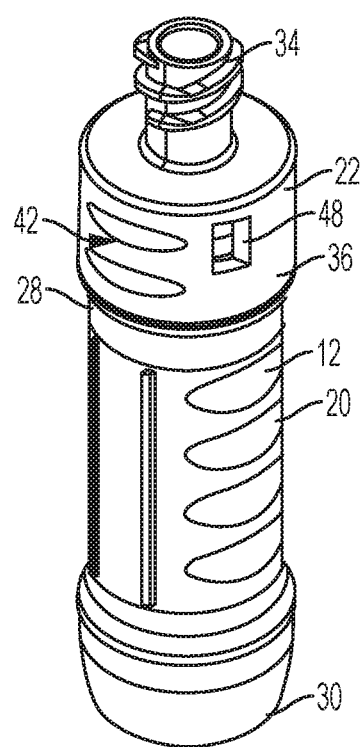
FIG. 2 is a perspective view of a syringe adapter according to one aspect of the present invention.
Figure 3:
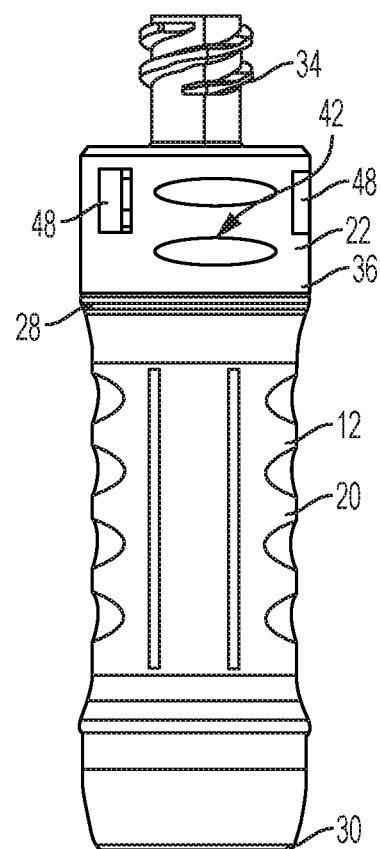
FIG. 3 is a front view of the syringe adapter of FIG. 2.
Figure 4:
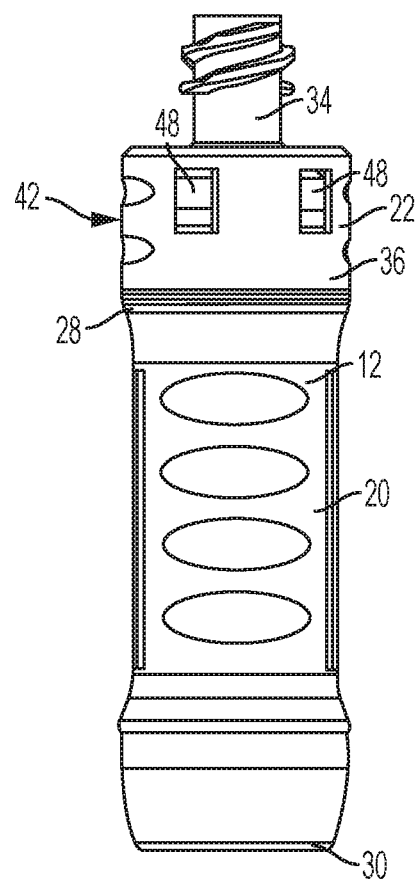
FIG. 4 is a right side view of the syringe adapter of FIG. 2.
Figure 5:
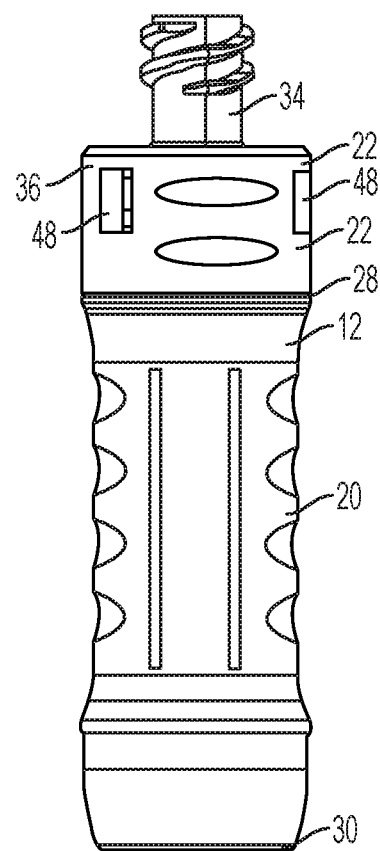
FIG. 5 is a rear view of the syringe adapter of FIG. 2.
Figure 6:
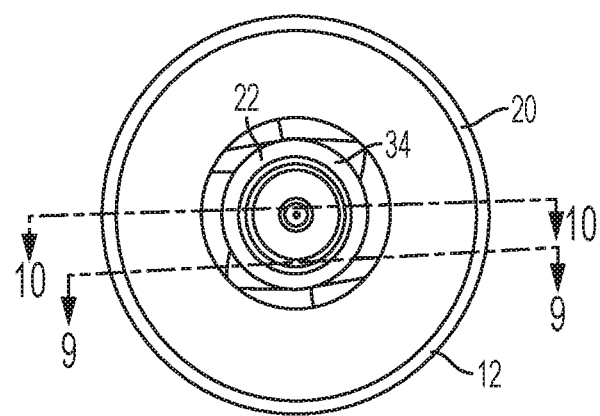
FIG. 6 is a top view of the syringe adapter of FIG. 2.
Figure 7:
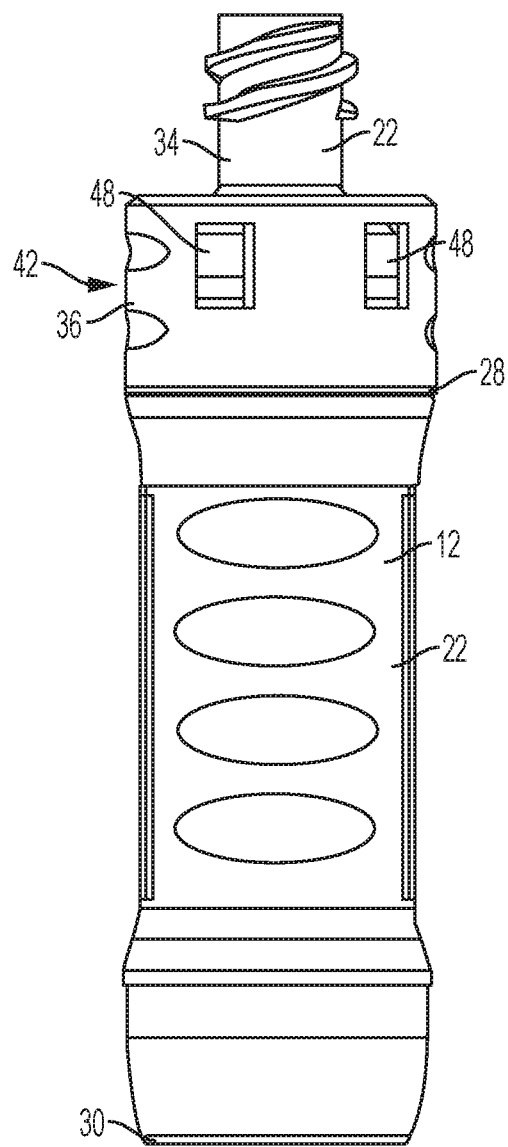
FIG. 7 is a left side view of the syringe adapter of FIG. 2.
Figure 8:
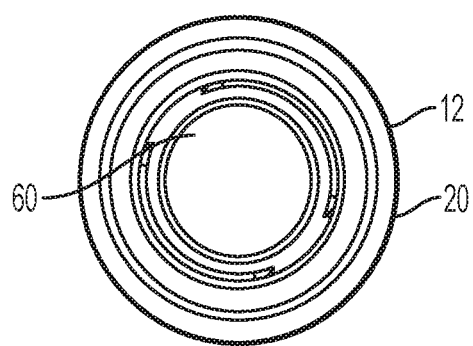
FIG. 8 is a bottom view of the syringe adapter of FIG. 2.
Figure 9:
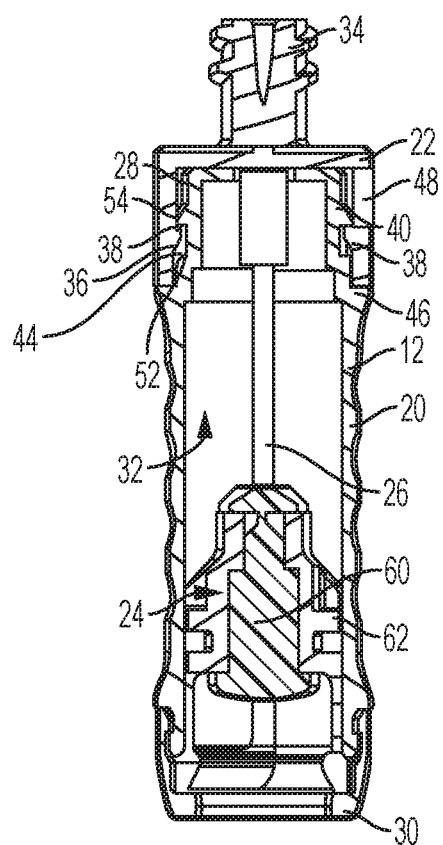
FIG. 9 is a cross-sectional view taken along line 9-9 shown in FIG. 6.
Figure 10:
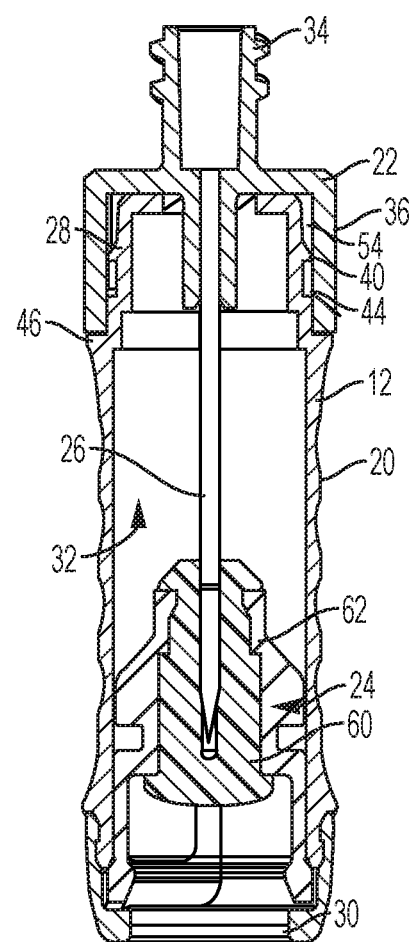
FIG. 10 is a cross-sectional view taken along line 10-10 shown in FIG. 6.
Figure 11:
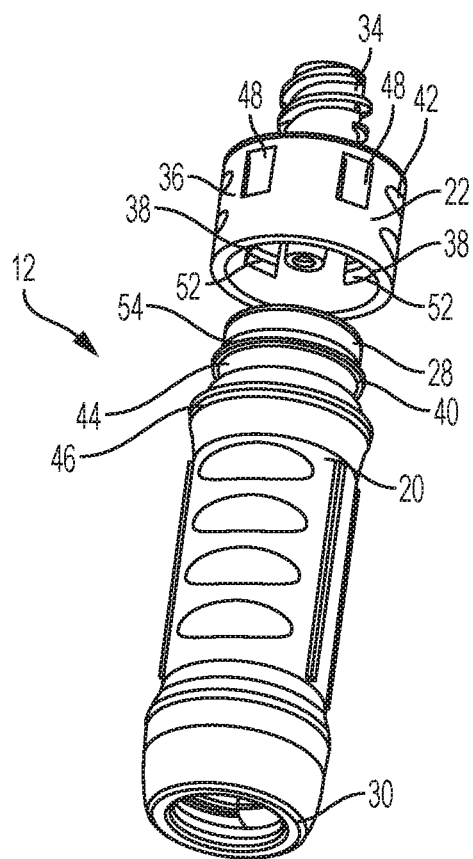
FIG. 11 is an exploded perspective view of the syringe adapter of FIG. 2.
Figure 12:
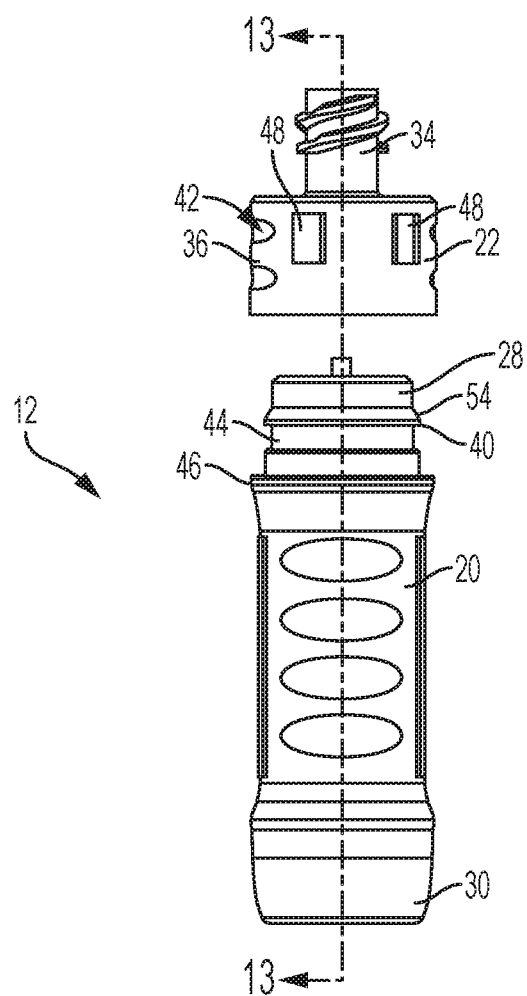
FIG. 12 is an exploded right side view of the syringe adapter of FIG. 2.

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

Referring to FIG. 1, one aspect of a system 10 includes a syringe adapter 12 and a patient connector 14. The syringe adapter 12 is configured to receive the patient connector 14 and form a sealed connection therewith. The syringe adapter 12 may be utilized to transfer fluid from a syringe (not shown) connected to the syringe adapter 12 to a patient line (not shown) connected to the patient connector 14. The syringe adapter 12 may also be utilized in connection with other components of a closed system transfer device including, but not limited to, a vial adapter, IV bag spike, and an IV line.

Referring to FIGS. 2-14, the syringe adapter 12 includes a housing 20, a connector body 22, a seal arrangement 24, and a cannula 26. The housing 20 has a first end 28 and a second end 30 and defines an interior space 32 that receives the seal arrangement 24. The connector body 22 is configured to be secured to a container, such as a syringe barrel. In particular, the connector body 22 includes a female luer connector 34 that is configured to mate with a male luer connector of a syringe barrel, although other suitable connector arrangements may be utilized. The connector body 22 is positioned adjacent to the first end 28 of the housing 20 and is secured to the housing 20. More specifically, the connector body 22 includes an axially extending skirt 36 that receives the first end 28 of the housing 20. The connector body 22 includes a plurality of locking projections 38 that extend radially inward from the skirt 36. The locking projections 38 of the connector body 22 cooperate with a retaining ring 40 that extends radially outward from the housing 20 adjacent to the first end 28 of the housing 20. The retaining ring 40 of the housing 20 extends circumferentially around the housing 20. The connector body 22 also includes a grip arrangement 42 configured to provide a gripping surface and visual indication of a location to grip the syringe adapter 12. The grip arrangement 42 is shown as two pairs of elliptical recesses, although other suitable grip arrangements may be utilized. Further, the connector body 22 may have a different color than the housing 20 or other visual indication that the connector body 22 is separate from the housing 20.

Upon assembly of the housing 20 to the connector body 22, the locking projections 38 of the connector body 22 are received within a recess 44 defined by the housing 20 below the retaining ring 40. The locking projections 38 of the connector body 22 engage the retaining ring 40 of the housing 20 to restrict axial movement of the connector body 22 relative to the housing 20 in a direction extending from the second end 30 of the housing 20 to the first end 28 of the housing 20. Further, the skirt 36 of the connector body 22 abuts a radially extending flange 46 of the housing 20 to restrict axial movement of the connector body 22 relative to the housing 20 in a direction extending from the first end 28 of the housing 20 to the second end 30 of the housing 20. The connector body 22, however, is rotatable relative to the housing 20 in both rotational directions about the longitudinal axis of the housing 20.

Figure 13:
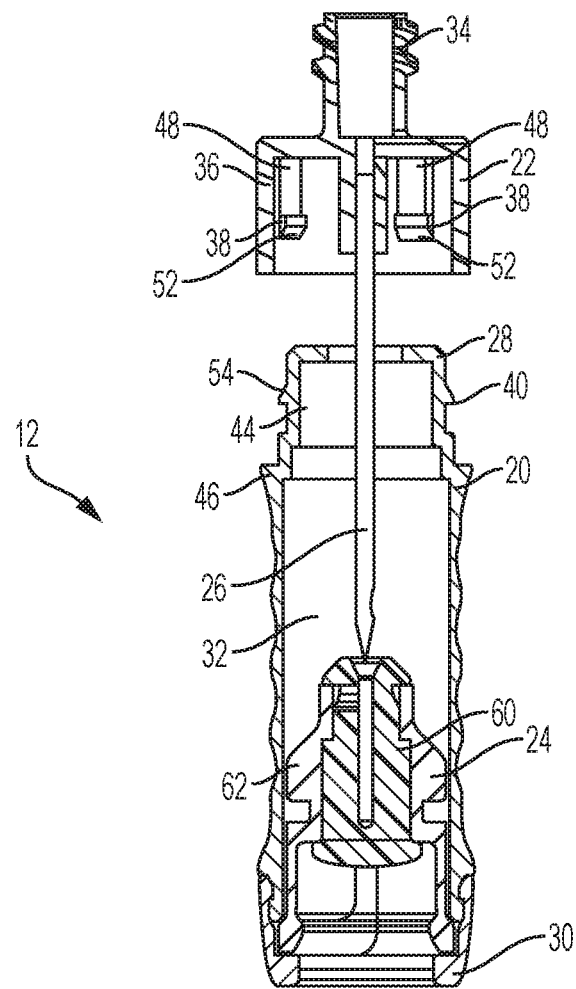
FIG. 13 is a cross-sectional view taken along line 13-13 shown in FIG. 12.
Figure 14:
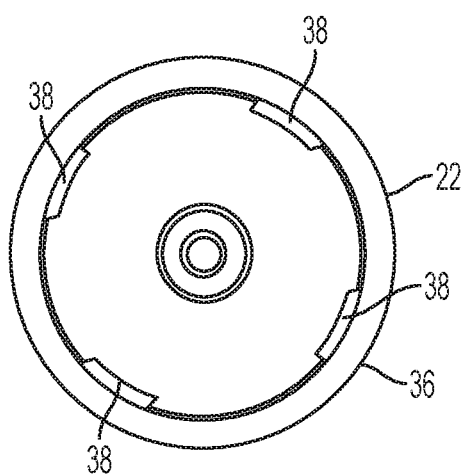
FIG. 14 is a bottom view of a connector body of the syringe adapter of FIG. 2 according to one aspect of the present invention.

Referring still to FIGS. 2-14, the connector body 22 includes four locking projections 38, although one or more locking projections 38 may be provided. The skirt 36 of the connector body 22 also defines a plurality of openings 48 adjacent to each of the locking projections 38. The locking projections 38 of the connector body 22 and the retaining ring 40 of the housing 20 each include an angled surface 52, 54 to facilitate assembly of the connector body 22 to the housing 20. As shown in FIG. 13, when the connector body 22 is moved onto the first end 28 of the housing 20, the angled surfaces 52 of the locking projections 38 will engage the angled surface 54 of the retaining ring 40 to bias the locking projections 38 of the connector body 22 radially outward. Continued movement of the connector body 22 onto the housing 20 causes the locking projections 38 to slide completely over the retaining ring 40 with the skirt 36 of the connector body 22 snapping back to its unbiased position. As discussed above, after assembly, the locking projections 38 of the connector body 22 are received by the recess 44 of the housing 20 below the retaining ring 40.

Referring to FIGS. 9, 10, 13, and 14, the connector body 22 receives the cannula 26 with the female luer connector 34 in fluid communication with the cannula 26. The cannula 26 is received within the interior space 32 of the housing 20 and is entirely surrounded by the housing 20. The seal arrangement 24 is positioned within the interior space 32 of the housing 20 and is moveable between the first and second ends 28, 30 of the housing 20. The seal arrangement 24 includes a membrane 60 and a collet 62 and is configured to cooperate with a mating connector, such as the patient connector 14, to provide for the sealed transfer of fluid through the cannula 26 into the mating connector. In use, the collet 62 receives the patient connector 14 with the membrane 60 engaging a membrane 64 on the patient connector 14. The collet 62 receives a portion of the patient connector 14 and moves the collet 62 toward the first end 28 of the housing 20, which secures the collet 62 to the patient connector 14 and causes the cannula 26 to pierce the membranes 60, 64 of the seal arrangement 24 and the patient connector 14. The seal arrangement 24 enables the sealed, closed transfer of fluids from a first container, such as a syringe, to a second container, such as an IV bag, by ensuring the membranes of the syringe adapter 12 and patient connector 14 are engaged during fluid transfer and by isolating the cannula 26 when fluids are not being transferred. Further, as noted above, the collet 62 is secured to a mating connector during use such that the syringe adapter 12 cannot be disengaged from the mating connector during fluid transfer to cause leakage of fluids being transferred. Although a specific seal arrangement is shown, the syringe adapter 12 may be utilized in connection with other suitable seal arrangements.

Referring again to FIGS. 2-14, during use of the syringe adapter 12, a syringe (not shown) is connected to the female luer connector 34 of the connector body 22 by gripping the connector body 22 to restrain rotational movement of the connector body 22 relative to the housing 20 while securing the syringe to the female luer connector 34. The connector body 22 may be restrained using the gripping arrangement 42. The syringe is removed in the same manner by gripping the connector body 22 to restrain rotational movement of the connector body 22 relative to the housing 20 and removing the syringe from the female luer connector 34. Accordingly, the syringe adapter 12 allows for purposeful connection and disconnection of the syringe to the syringe adapter 12 while preventing accidental disconnection by allowing the connector body 22 to rotate relative to the housing 20. For example, when the syringe adapter 12 is connected to an IV line via the patient connector 14, movement of the IV line is not translated to the connector body 22, which can torque the connector body 22 and accidentally disconnect a syringe or other container from the connector body 24.

Figure 15:
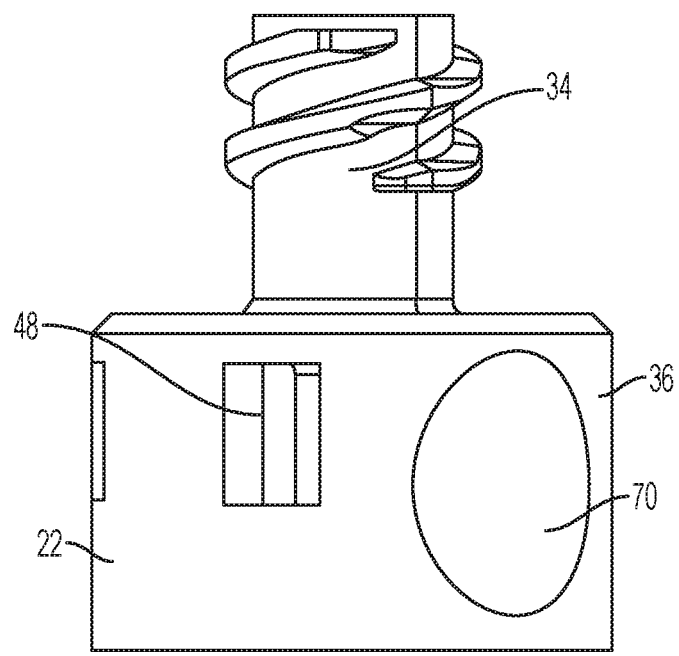
FIG. 15 is a front view of a connector body according to a second aspect of the present invention.
Figure 16:
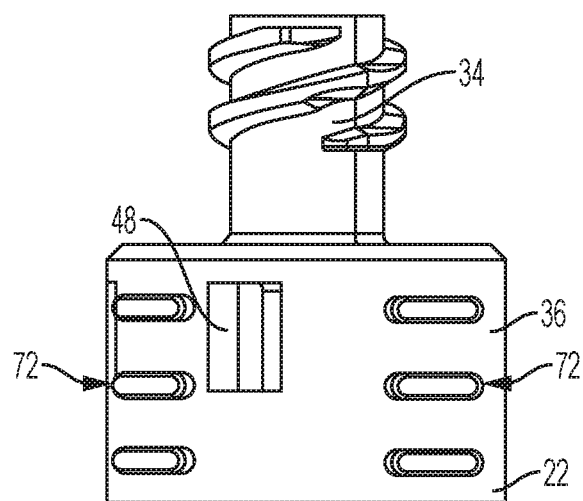
FIG. 16 is a front view of a connector body according to a third aspect of the present invention.

Referring to FIGS. 15 and 16, further aspects of the grip arrangement 42 are shown. The grip arrangement 42 may be a spherical recess 70 defined by the skirt 36 of the connector body 22 (FIG. 15) or may be a plurality of generally rectangular projections 72 extending radially outward from the skirt 36 of the connector body 22 (FIG. 16). As noted above, other suitable grip arrangements 42 may be provided to improve the grip ergonomics and various colors and textures can be utilized to reinforce that the connector body 22 is separate from the housing 20 and rotatable relative to the housing 20 thereby requiring gripping of the connector body 22 for attachment and detachment of the syringe from the female luer connector 34. The grip arrangement 42 may have different numbers, shapes, and sizes and may also utilize a logo or other branding for the grip arrangement 42.

Although the invention has been described in detail for the purpose of illustration based on what is currently considered to be the most practical and preferred aspects, it is to be understood that such detail is solely for that purpose and that the invention is not limited to the disclosed aspects, but, on the contrary, is intended to cover modifications and equivalent arrangements that are within the spirit and scope of the appended claims. For example, it is to be understood that the present invention contemplates that, to the extent possible, one or more features of any aspect can be combined with one or more features of any other aspect.

The invention claimed is:

1. A syringe adapter comprising:
   a housing having a first end and a second end and defining an interior space;
   a seal arrangement received within the interior space of the housing;
   a connector body positioned adjacent to the first end of the housing and configured to be connected with a syringe barrel, the connector body secured to the housing and rotatable relative to the housing in first and second directions, the connector body is axially fixed relative to the housing; and
   a cannula secured to the connector body, the seal arrangement configured to cooperate with the cannula to provide a sealed transfer of fluids through the cannula to a mating connector,
   wherein the connector body includes a grip arrangement configured to provide a gripping surface and visual indication of a location to grip the syringe adapter,
   wherein the connector body comprises a skirt extending in an axial direction, the skirt of the connector body receiving the first end of the housing, and
   wherein the grip arrangement is at least one recess defined by the skirt of the connector body.

2. The syringe adapter of claim 1, wherein the connector body further has a threaded female luer extending from the skirt away from the housing, and wherein the at least one recess is spaced from the threaded female luer.

3. The syringe adapter of claim 1, wherein the at least one recess is at least one spherical recess.

4. The syringe adapter of claim 1, wherein the at least one recess is a plurality of elliptical recesses.

5. The syringe adapter of claim 1, wherein the at least one recess is a plurality of recesses.

6. The syringe adapter of claim 1, wherein the connector body further comprises a plurality of projections that extend radially inward from the skirt, and a corresponding plurality of openings each adjacent to a corresponding one of the plurality of projections.

7. The syringe adapter of claim 1, wherein the cannula is entirely positioned within the housing.

8. The syringe adapter of claim 1, wherein the seal arrangement is moveable within the housing, the seal arrangement comprising a membrane.

9. A syringe adapter comprising:
   a housing having a first end and a second end and defining an interior space;
   a seal arrangement received within the interior space of the housing;
   a connector body positioned adjacent to the first end of the housing and configured to be connected with a syringe barrel, the connector body secured to the housing and rotatable relative to the housing in first and second directions, the connector body is axially fixed relative to the housing; and
   a cannula secured to the connector body, the seal arrangement configured to cooperate with the cannula to provide a sealed transfer of fluids through the cannula to a mating connector,
   wherein the connector body includes a grip arrangement configured to provide a gripping surface and visual indication of a location to grip the syringe adapter,
   wherein the connector body comprises a skirt extending in an axial direction, the skirt of the connector body receiving the first end of the housing, and
   wherein the grip arrangement is a plurality of projections extending radially outward from the skirt of the connector body.

10. The syringe adapter of claim 9, wherein the connector body further has a threaded female luer extending from the skirt away from the housing, and wherein each of the plurality of projections are spaced from the threaded female luer.

11. The syringe adapter of claim 9, wherein the connector body further comprises a plurality of projections that extend radially inward from the skirt, and a corresponding plurality of openings each adjacent to a corresponding one of the plurality of projections that extend radially inward from the skirt.

12. The syringe adapter of claim 9, wherein the plurality of projections are each generally rectangular-shaped.

13. A syringe adapter comprising:
   a housing having a first end and a second end and defining an interior space;
   a seal arrangement received within the interior space of the housing;
   a connector body positioned adjacent to the first end of the housing and configured to be connected with a syringe barrel, the connector body secured to the housing and rotatable relative to the housing in first and second directions, the connector body is axially fixed relative to the housing; and
   a cannula secured to the connector body, the seal arrangement configured to cooperate with the cannula to provide a sealed transfer of fluids through the cannula to a mating connector,
   wherein the connector body includes a grip arrangement configured to provide a gripping surface and visual indication of a location to grip the syringe adapter, and
   wherein the connector body is a different color than the housing.

14. A syringe adapter comprising:
   a housing having a first end and a second end and defining an interior space, the housing comprising a retaining ring;
   a seal arrangement received within the interior space of the housing, the seal arrangement moveable within the housing and comprising a membrane;
   a connector body positioned adjacent to the first end of the housing and configured to be connected with a syringe barrel, the connector body comprising a locking projection, the locking projection of the connector body cooperating with the retaining ring of the housing to secure the connector body to the housing, the connector body is rotatable relative to the housing in first and second directions, the locking projection engaging the retaining ring to restrict axial movement of the connector body relative to the housing; and a cannula secured to the connector body, the seal arrangement configured to cooperate with the cannula to provide a sealed transfer of fluids through the cannula to a mating connector, wherein the connector body includes a grip arrangement configured to provide a gripping surface and visual indication of a location to grip the syringe adapter, wherein the connector body comprises a skirt extending in an axial direction, the skirt of the connector body receiving the first end of the housing, and wherein the grip arrangement is at least one recess defined by the skirt of the connector body.

15. The syringe adapter of claim 14, wherein the connector body further has a threaded female luer extending from the skirt away from the housing, and wherein the at least one recess is spaced from the threaded female luer.

16. A syringe adapter comprising:
a housing having a first end and a second end and defining an interior space, the housing comprising a retaining ring;
a seal arrangement received within the interior space of the housing, the seal arrangement moveable within the housing and comprising a membrane;
a connector body positioned adjacent to the first end of the housing and configured to be connected with a syringe barrel, the connector body comprising a locking projection, the locking projection of the connector body cooperating with the retaining ring of the housing to secure the connector body to the housing, the connector body is rotatable relative to the housing in first and second directions, the locking projection engaging the retaining ring to restrict axial movement of the connector body relative to the housing; and
a cannula secured to the connector body, the seal arrangement configured to cooperate with the cannula to provide a sealed transfer of fluids through the cannula to a mating connector, wherein the connector body includes a grip arrangement configured to provide a gripping surface and visual indication of a location to grip the syringe adapter, wherein the connector body comprises a skirt extending in an axial direction, the skirt of the connector body receiving the first end of the housing, and wherein the grip arrangement is a plurality of projections extending radially outward from the skirt of the connector body.

17. The syringe adapter of claim 16, wherein the connector body further has a threaded female luer extending from the skirt away from the housing, and wherein each of the plurality of projections extending radially outward from the skirt are spaced from the threaded female luer.

18. The syringe adapter of claim 16, wherein the plurality of projections extending radially outward from the skirt are each generally rectangular-shaped.

* * * * *